US 11,624,749 B2

(12) United States Patent
Bryden et al.

(10) Patent No.: US 11,624,749 B2
(45) Date of Patent: *Apr. 11, 2023

(54) COATING OF AEROSOL PARTICLES USING AN ACOUSTIC COATER

(71) Applicant: Zeteo Tech, Inc., Sykesville, MD (US)

(72) Inventors: Wayne A. Bryden, Sykesville, MD (US); Charles J. Call, Sykesville, MD (US)

(73) Assignee: ZeteoTech, Inc., Sykesville, MD (US)

( * ) Notice: Subject to any disclaimer, the term of this patent is extended or adjusted under 35 U.S.C. 154(b) by 85 days.

This patent is subject to a terminal disclaimer.

(21) Appl. No.: 16/784,247

(22) Filed: Feb. 7, 2020

(65) Prior Publication Data
US 2020/0241000 A1 Jul. 30, 2020

Related U.S. Application Data

(63) Continuation of application No. 15/755,063, filed as application No. PCT/US2016/048395 on Aug. 24, 2016, now Pat. No. 10,598,668.

(60) Provisional application No. 62/378,153, filed on Aug. 22, 2016, provisional application No. 62/209,320, filed on Aug. 24, 2015.

(51) Int. Cl.
*G01N 33/68* (2006.01)
*B05B 17/06* (2006.01)
*G01N 1/30* (2006.01)
*G01N 1/38* (2006.01)
*H01J 49/16* (2006.01)
*G01N 1/28* (2006.01)
*G01N 15/10* (2006.01)
*H01J 49/04* (2006.01)
*H01J 49/40* (2006.01)

(Continued)

(52) U.S. Cl.
CPC ........ *G01N 33/6851* (2013.01); *B05B 17/06* (2013.01); *G01N 1/28* (2013.01); *G01N 1/30* (2013.01); *G01N 1/38* (2013.01); *G01N 15/10* (2013.01); *H01J 49/0445* (2013.01); *H01J 49/164* (2013.01); *H01J 49/40* (2013.01); *B06B 2201/77* (2013.01); *G01N 2001/002* (2013.01); *G01N 2001/302* (2013.01); *G01N 2015/0046* (2013.01); *G01N 2560/00* (2013.01)

(58) Field of Classification Search
CPC .......................... G01N 33/6851; B05B 17/06
See application file for complete search history.

(56) References Cited

U.S. PATENT DOCUMENTS 6,579,718 B1 * 6/2003 Yue ........................ C09B 23/105
436/86
7,170,052 B2 * 1/2007 Furutani .............. G01N 27/622
250/281

(Continued)

FOREIGN PATENT DOCUMENTS

WO    WO2015/074959    *  5/2015    ............... B05B 7/04

*Primary Examiner* — Dah-Wei D. Yuan
*Assistant Examiner* — Andrew J Bowman
(74) *Attorney, Agent, or Firm* — Paradice & Li LLP; Anand S. Chellappa

(57) ABSTRACT

Coating materials such as MALDI matrix solutions are aerosolized and are used to coat analyte particles in an acoustic coater. Methods and devices for coating analyte particles in real time are disclosed. The coating improves the detection and quantification of the analyte particles using analytical instruments such as an aerosol time of flight mass spectrometer.

11 Claims, 8 Drawing Sheets

(51) Int. Cl.
  *G01N 15/00* (2006.01)
  *G01N 1/00* (2006.01)

(56) References Cited

U.S. PATENT DOCUMENTS

| | | | |
|---|---|---|---|
| 8,409,870 B2* | 4/2013 | Van Wuijckhuijse | ....................... H01J 49/0418 250/282 |
| 2003/0020011 A1* | 1/2003 | Anderson | ............... H01J 49/40 250/288 |
| 2005/0017102 A1* | 1/2005 | Shekarriz | ................ B05B 5/004 239/690 |
| 2009/0061089 A1* | 3/2009 | King | .................... B01L 3/0268 427/255.25 |
| 2010/0297635 A1* | 11/2010 | Olin | ....................... A61B 5/411 435/7.1 |
| 2011/0014235 A1* | 1/2011 | Berninger | ............... A61K 39/39 977/773 |
| 2014/0272172 A1* | 9/2014 | Zhamu | ................ H01L 31/1884 427/457 |

* cited by examiner

```
                          ┌──────────────────┐
                          │ Providing MALDI  │                    400
                          │ Matrix Solution  │                 ↙┄┄┄
                          │ 401              │
                          └────────┬─────────┘
                                   │
                                   ▼
                          ┌──────────────────┐
                          │ Nebulizing       │       Type 1 aerosol
                          │ MALDI matrix     │┄┄┄┄┄┄┄┄
                          │ 402              │
                          └────────┬─────────┘
                                   │
┌──────────────┐   ┌──────────────┐│  ┌────────────────────────────────────┐
│ Coating in   │   │ Mixing       ││  │ Providing Type 2 Sampled Aerosol   │
│ Acoustic     │◄──│ Component    │◄─ │ (Analyte)                          │
│ Coater       │   │ (optional)   │   │ 403                                │
│ 405          │   │ 404          │   │                                    │
└──────┬───────┘   └──────────────┘   └────────────────────────────────────┘
       │
       ▼
┌──────────────┐
│ Drying       │
│ (optional)   │
│ 406          │
└──────┬───────┘
       │
       ▼
To analytical instrument
such as a mass spectrometer
```

FIG. 4

MALDI aerosol
+ analyte aerosol analyte aerosol

FIG. 5

```
┌─────────────────┐
│ Providing MALDI │
│ Matrix Solution │                                    500
│ 501             │                                   ↙
└────────┬────────┘
         ▼
┌─────────────────┐      ┌─────┐
│ Nebulizing MALDI│◄─────│ Air │
│ matrix 502      │      └─────┘
└────────┬────────┘
         │                        ──────── Type 1 aerosol
         │
         │        ┌──────────────────────────────┐
         │◄───────│ Providing Type 2 Aerosol     │
         │        │ (Analyte) Sample             │
         │        │ 503                          │
         ▼        └──────────────────────────────┘
┌─────────────────┐
│ Mixing Component│
│ (optional)      │
│ 504             │
└────────┬────────┘
         ▼
┌─────────────────┐
│ Coating in      │
│ Acoustic Coater │
│ 505             │
└────────┬────────┘
         ▼
┌─────────────────┐
│ Drying          │
│ (optional)      │
│ 506             │
└────────┬────────┘
         ▼
To analytical instrument
such as a mass spectrometer
```

FIG. 6

COATING OF AEROSOL PARTICLES USING AN ACOUSTIC COATER

RELATED APPLICATIONS

This application is a Continuation of U.S. patent application Ser. No. 15/755,063, filed Feb. 24, 2018, which is a U.S. National Stage Application of International Application No. PCT/US2016/48395, filed Aug. 24, 2016, which is related to and claims the benefit of and priority to U.S. Provisional Application No. 62/209,320, filed Aug. 24, 2015, and entitled "Coating of Aerosol Particles Using An Acoustic Coater," and U.S. Provisional Application No. 62/378,153, filed Aug. 22, 2016, and entitled "Coating of Aerosol Particles Using An Acoustic Coater," the entire disclosures of which are incorporated herein by reference in their entireties.

FEDERALLY SPONSORED RESEARCH AND DEVELOPMENT

Not applicable.

FIELD

This disclosure relates to methods and devices for coating aerosol analyte particles using an acoustic coater to improve the detection and quantification of the analyte particles. More particularly, but not by way of limitation, the disclosure relates to methods and devices for applying a coating of a MALDI matrix solution to bio aerosol particles prior to their analysis in an aerosol time-of-flight mass spectrometer.

BACKGROUND

In 2002, the Nobel Prize in chemistry was shared by Koichi Tanaka for the concept of "matrix assisted" laser desorption ionization (MALDI), which allowed large molecules to be analyzed intact using mass spectrometry. In this technique, the target particle (analyte) is coated by a matrix chemical, which preferentially absorbs light (often ultraviolet wavelengths) from a laser. In the absence of the matrix, the biological molecules would decompose by pyrolysis when exposed to a laser beam in a mass spectrometer. The matrix chemical also transfers charge to the vaporized molecules, creating ions that are then accelerated down a flight tube by the electric field (Brown, 1995; Knochenmuss, 1996). Microbiology and proteomics have become major application areas for mass spectrometry; examples include the identifaction of bacteria (Carbonnelle, 2010), discovering chemical structures, and deriving protein functions (Karas, 1987; Cotter, 1994, 1997). Danielewicz and co-workers (2011) report the use of MALDI mass spectrometry for lipid profiling of algae.

The coated analyte particles, which are often intact microbes are then analyzed using MALDI Time of Flight (TOF) mass spectrometry. FIG. 1 shows the "conventional" MALDI TOF mass spectrometry process. A liquid, usually comprised of an acid, such as tri-fluoro-acetic acid (TFA), and a MALDI matrix chemical such as alpha-cyano-4-hydroxycinnamic acid, is dissolved in a solvent and added to the analyte. Solvents include acetonitrile, water, ethanol, and acetone. TFA is normally added to suppress the influence of salt impurities on the mass spectrum of the analyte. Water enables hydrophilic proteins to dissolve, and acetontrile enables the hydrophobic proteins to dissolve. The MALDI matrix solution is spotted on to the analyte on a MALDI plate 10 to yield a uniform homogenous layer of MALDI matrix material on the analyte. The solvents vaporize, leaving only the recrystallized matrix with the analyte spread through the matrix crystals. The acid partially degrades the cell membrane of the analyte making the proteins available for ionization and analysis in a TOF mass spectrometer. The coated plate is then analyzed in a TOF mass spectrometer.

Other MALDI matrix materials include 3,5-dimethoxy-4-hydroxycinnamic acid (sinapinic acid), α-cyano-4-hydroxycinnamic acid (α-cyano or α-matrix) and 2,5-dihydroxybenzoic acid (DHB) as described in U.S. Pat. No. 8,409,870.

The accuracy of MALDI mass spectrometry can be higher than that obtainable using traditional chemical techniques. Carbonelle et al. (2010) provides an excellent analysis of MALDI mass spectrometry bacterial identification in clinical microbiological laboratories, and conclude that the identification of bacteria, yeast, and fungi by MALDI mass spectrometry was the fastest technique for routine microbiology. Cherkaoui and co-workers (2010) compared mass spectrometry with conventional biochemical test system identifications for clinically relevant bacteria. Discordant results were resolved with "gold standard" 16S rRNA gene sequencing. The first MALDI mass spectrometry system (Bruker) gave high-confidence identifications for 680 isolates, of which 674 (99.1%) were correct; the second mass spectrometry system (Shimadzu) gave high-confidence identifications for 639 isolates, of which 635 (99.4%) were correct. FIG. 2 shows typical spectra for whole colonies of different species. It should be noted that the same species can yield differing spectra on account of the growing conditions, the growth phase, and the matrix used to obtain the spectra. However, microbial indentification is accurate, owing to the fact that many of the peaks associated with protein biomarkers are preserved.

Conventional MALDI mass spectrometry can be used to analyze cultured bacteria samples, but is generally not amenable to analysis of single organisms. Furthermore, if the sample contains a mixture of bacteria, the spectra generated would contain the characteristics of all of the species in the sample; hence, the spectra are cluttered and difficult to deconvolute. Both of these issues can be overcome by culturing the sample, which creates an abundance of the target bacteria in a colony. However, this approach has two drawbacks, namely, (1) it works only for culturable targets, and (2) because sample preparation occurs off-line in the lab, it incurs an associated labor cost and is time intensive. The conventional MALDI mass spectrometry is not amenable to real time analysis of bioaerosols in a sample, for example, biological contaminant particles in ambient air.

Aerosol Time of Flight Mass Spectrometry (ATOFMS) can be used to perform real-time measurements of sampled particles or aerosols. Measurements of individual particle composition and size made by ATOFMS provide valuable insights into the sources of these particles. ATOFMS has been used for the detection of aerosols and health effects studies. For example, TSI, Inc. (Shoreview, Minn.) has manufactured mass spectrometers to yield particle size and composition information for particles that range from 0.03 to 3 micrometers in size. The total inlet air flow rate to the spectrometer is 0.1 L/min. Ambient aerosol particle loadings are tyically 10 to 1000 particles per mL for particles in the 0.03 to 3 micrometers size range. ATOFMS uses an aerodynamic sizing technique to sample and size particles based on each particle's transit time between two laser beams. The particles are then illuminated using a UV laser.

The laser vaporizes and ionizes at least some of the molecules which comprise each illuminated particle, thus generating ions with specific mass to charge ratios (m/z). The electric field inside the mass spectrometer accelerates these charged particles and measures the time-of-flight to a detector to yield a unique fingerprint spectrum. This measured spectrum can be compared with database information to provide information on chemical composition. ATOFMS quickly identifies the specific chemical compounds that make up each particle. Hundreds or perhaps thousands of particles can be analyzed per second using this technique, providing real-time information on the nature of the aerosol.

Particles comprising proteins and other bio-organic molecules (bioaerosols) however tend to absorb the intense UV laser light and decompose by pyrolysis, making the ATOFMS analysis technique ineffective. In order to analyze bioaerosols, each of the particles in the aerosol must be coated with the MALDI matrix. MALDI matrix coating of analyte aerosol particles prior to introduction into the ATOFMS was first described by Stowers (2000), and then by van Wuij ckhuij se (2004). The advantage of analyzing particles in a bioaerosol one particle at a time is that each particle is a representative of the "pure sample" of the constituent proteins and other high molecular weight molecules. In the case of a single airborne bacterium, it represents a "pure culture" of that one organism. The ambient aerosol (analyte) is first passed through a hot zone which contains a relative high vapor pressure MALDI matrix material. The matrix vapor mixes with the aerosol by diffusion and then enters into a cool zone. Here, the matrix condenses out of the vapor phase to form a matrix aerosol, some of which may coat the analyte aerosol particles. The analyte aerosol is dispersed within the matrix aerosol, but the mean particle diameter is considerably less than that of the matrix aerosol. The analyte aerosol particle typically has a particle size of between 0.5 to 15 micrometers. The analyte aerosol is now "vapor coated" with matrix. Mass spectrometry fingerprints obtained using the aerosol MALDI MS technique closely resemble those obtained from conventional MALDI mass spectrometry. For microbes, the fingerprint can be associated with specific proteins present in a particular organism. FIG. 3 compares measurements for single spores (diameter of about 1 micrometer) of acillus atrophaeus by van Wuijckhuij se (2010), with measurements from a conventional MALDI mass spectrometry (Hathout, 1999). As can be seen, key biomarkers are preserved across platforms. With conventional MALDI mass spectrometry, the fingerprint is obtained by co-averaging hundreds of spectra obtained from a single clump comprised of thousands of spores. In contrast, with aerosol MALDI mass spectrometry, the fingerprint was obtained by averaging 135 single-spore spectra.

The vapor coating technique of van Wuijckhuij se et al. has some notable shortcomings. First, vapor deposition of the conventional MALDI matrix chemical may not accurately simulate and replicate the homogeneous and uniform coating obtained during conventional liquid coating of the analyte (in FIG. 1). Further, as disclosed in U.S. Pat. No. 8,409,870, the technique required the use of a customized MALDI matrix material 2-mercapto-4, 5-dialkylheteroarene and an alcohol. Suitable alcohols included methanol, ethanol and propanol. This is a significant limitation in that the conventional matrix chemicals, such as alpha-Cyano-4-hydroxycinnamic acid, 3,5-dimethoxy-4-hydroxycinnamic acid (sinapinic acid), and 2,5-dihydroxybenzoic acid (DHB) are prone to degrade during the vaporization step of the vapor deposition technique.

Therefore, a real-time and "on-the-fly" aerosol coater, capable of producing a coating of matrix material on the analyte particle, and preferably while using conventional matrix materials is desired.

SUMMARY

The present disclosure relates to methods and devices for coating aerosol analyte particles using an acoustic coater to improve the detection and quantification of the analyte particles. More particularly, but not by way of limitation, the present disclosure relates to methods and devices for applying a coating of a MALDI matrix solution to bio aerosol particles prior to their analysis in an aerosol time-of-flight mass spectrometer. Aerosol generally means a suspension of particles dispersed in air or gas. Disclosed herein are aspects to perform real time "on-the-fly" MALDI matrix coating of aerosol particles. "On-the-fly" means that the particles comprising the aerosol are not collected onto a surface (for example, onto the surface of a MALDI plate) or into a liquid as a step in the coating process. More specifically, disclosed herein are MALDI matrix coaters and methods that employ an acoustic treatment of aerosolized MALDI matrix and analyte aerosol particles to obtain MALDI coated analyte particles, prior to analysis using analytical instruments such as an ATOFMS.

The present disclosure provides methods for coating sampled aerosol particles comprising aerosolizing a coating material to form a first aerosol comprising liquid particles, providing a sampled aerosol containing analyte particles to form a second aerosol, providing an acoustic coater to receive the first and second aerosols and providing an acoustic field to the acoustic coater to urge the first aerosol to impinge upon the second aerosol to form a coating of the first aerosol on the second aerosol particles. The coating material comprises a MALDI matrix solution. The MALDI matrix solution comprises a stain for staining the analyte particles. The MALDI matrix solution comprises at least one of 2,5-dihydroxybenzoic acid, alpha-cyano-4-hydroxycinnamic acid, 3,5-dimethoxy-4-hydroxycinnamic acid, 2-mercapto-4, 5-dialkylheteroarene, 1,8-dihydroxyanthracen-9 (10H)-one, 3-methoxy-4-hydroxycinnamic acid, 2,4,6-trihydroxyacetophenone, 2-(4-hydroxyphenylazo)-benzoic acid, trans-3-indoleacrylic acid, 4-hydroxy-3-methoxybenzoic acid, 6-aza-2-thiothymine, 2-amino-4-methyl-5-nitropyridine, 4-nitroaniline, 1,5-diaminonaphthalene, 5-fluorosalicylic acid, 5-chlorosalicylic acid, 5-bromosalicylic acid, 5-iodosalicylic acid, 5-methylsalicylic acid, 5-aminosalicylic acid, and 1,8-diaminonaphthalene. Further, the MALDI matrix solution comprises at least one of acetonitrile, water, ethanol, methanol, propanol, acetone, chloroform, isopropyl alcohol, tetrahydrofuran, and toluene. The MALDI matrix solution comprises at least one of hydrochloric acid, trifluroacetic acid, formic acid, and acetic acid. Optionally, the methods include a mixing step wherein the first aerosol is mixed with second aerosol prior to entering said acoustic coater. A sheath fluid is optionally added during the mixing step to reduce or eliminate deposition of the aerosols. Optionally, the methods comprise a drying step to dry said coated second aerosol particles. The sampled aerosol comprises at least one of exhaled breath particles, material collected from the head space of a fermentor, and collected from ambient air.

The present disclosure provides devices for coating sampled aerosol particles with MALDI matrix solution comprising a nebulizer to aerosolize the MALDI matrix solution to form a first aerosol of liquid particles, means for capturing a sampled aerosol containing analyte particles to form a second aerosol, and an acoustic coater configured to be in fluid communication with the nebulizer and the capturing means to receive the first aerosol and the second aerosol, wherein an acoustic field is applied to the acoustic coater to urge said first aerosol to impinge upon particles of the second aerosol to form a coating of first aerosol on the second aerosol particles. The MALDI matrix solution comprises a stain for staining the analyte particles. The MALDI matrix solution comprises at least one of 2,5-dihydroxybenzoic acid, alpha-cyano-4-hydroxycinnamic acid, 3,5-dimethoxy-4-hydroxycinnamic acid, 2-mercapto-4, 5-dialkylheteroarene, 1,8-dihydroxyanthracen-9(10H)-one, 3-methoxy-4-hydroxycinnamic acid, 2,4,6-trihydroxyacetophenone, 2-(4-hydroxyphenylazo)-benzoic acid, trans-3-indoleacrylic acid, 4-hydroxy-3-methoxybenzoic acid, 6-aza-2-thiothymine, 2-amino-4-methyl-5-nitropyridine, 4-nitroaniline, 1,5-diaminonaphthalene, 5-fluorosalicylic acid, 5-chlorosalicylic acid, 5-bromosalicylic acid, 5-iodosalicylic acid, 5-methylsalicylic acid, 5-aminosalicylic acid, and 1,8-diaminonaphthalene. Further, the MALDI matrix solution comprises at least one of acetonitrile, water, ethanol, methanol, propanol, acetone, chloroform, isopropyl alcohol, tetrahydrofuran, and toluene. The MALDI matrix solution comprises at least one of hydrochloric acid, trifluroacetic acid, formic acid, and acetic acid. Optionally, the devices comprise a mixing chamber wherein the first aerosol is mixed with second aerosol prior to entering said acoustic coater. A sheath fluid is optionally added in the mixing chamber to reduce or eliminate deposition of the aerosols. Optionally, the devices comprise suitable means to heat the coated analyte aerosol to accelerate solvent evaporation.

The present disclosure provides for methods for identifying the particles present in a sampled aerosol, comprising providing MALDI matrix coated sampled aerosol particles according and routing said coated aerosol particles to a mass spectrometer. In one aspect, the mass spectrometer is an aerosol time of flight mass spectrometer (ATOFMS).

The present disclosure provides methods for identifying the molecules present in a sampled aerosol comprising providing MALDI matrix coated sampled aerosol, coating a MALDI plate with MALDI matrix coated aerosol, and, analyzing the coated plate in a mass spectrometer. Optionally, the methods comprise a drying step to dry said coated second aerosol particles prior to analyzing in a mass spectrometer.

The present disclosure provides for methods for coating aerosol particles with a coating material comprising aerosolizing the coating material to form a first aerosol, providing an aerosol containing analyte particles to form a second aerosol, providing an acoustic coater to receive the first aerosol and the second aerosol, and providing an acoustic field to the acoustic coater to urge the first aerosol to impinge upon particles of the second aerosol to form a coating of the first aerosol on particles of the second aerosol. The coating material comprises at least one of solid particles and a mixture of solid particles. The solid particles comprise metal powders of particles size less than 1 micrometer. The mixture comprises metal and non-metal powders. The metal powders comprise cobalt powders.

The present disclosure provides devices for identifying the particles present in a sampled aerosol comprising a device for providing MALDI matrix coated sampled aerosol particles, and a mass spectrometer. The mass spectrometer is an aerosol time of flight mass spectrometer (ATOFMS).

The present disclosure provides a method for coating analyte particles found in a liquid sample comprising aerosolizing a coating material to form a first aerosol comprising liquid particles, aerosolizing a liquid sample to form a second aerosol comprising analyte particles, providing an acoustic coater to receive said first aerosol and said second aerosol, and providing an acoustic field to said acoustic coater to urge said first aerosol to impinge upon particles of said second aerosol to form a coating of first aerosol on said analyte particles. The coating material comprises MALDI matrix solution.

The present disclosure provides a method for identifying analyte particles present found in a liquid sample comprising, providing MALDI matrix coated analyte particles and, analyzing said coated analyte particles in a mass spectrometer. The mass spectrometer is an aerosol time of flight mass spectrometer (ATOFMS).

Other features and advantages of the present disclosure will be set forth, in part, in the descriptions which follow and the accompanying drawings, wherein different aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

BRIEF DESCRIPTION OF THE DRAWINGS

The foregoing aspects and many of the attendant advantages of this disclosure will become more readily appreciated as the same becomes better understood by reference to the following detailed description, when taken in conjunction with the accompanying drawings, wherein:

FIG. 4. Schematic diagram of one aspect of the acoustic coating process.

FIG. 5. Schematic diagram of an exemplary nebulizer system.

FIG. 6. Schematic diagram of another aspect of the acoustic coating process.

Figure 1:
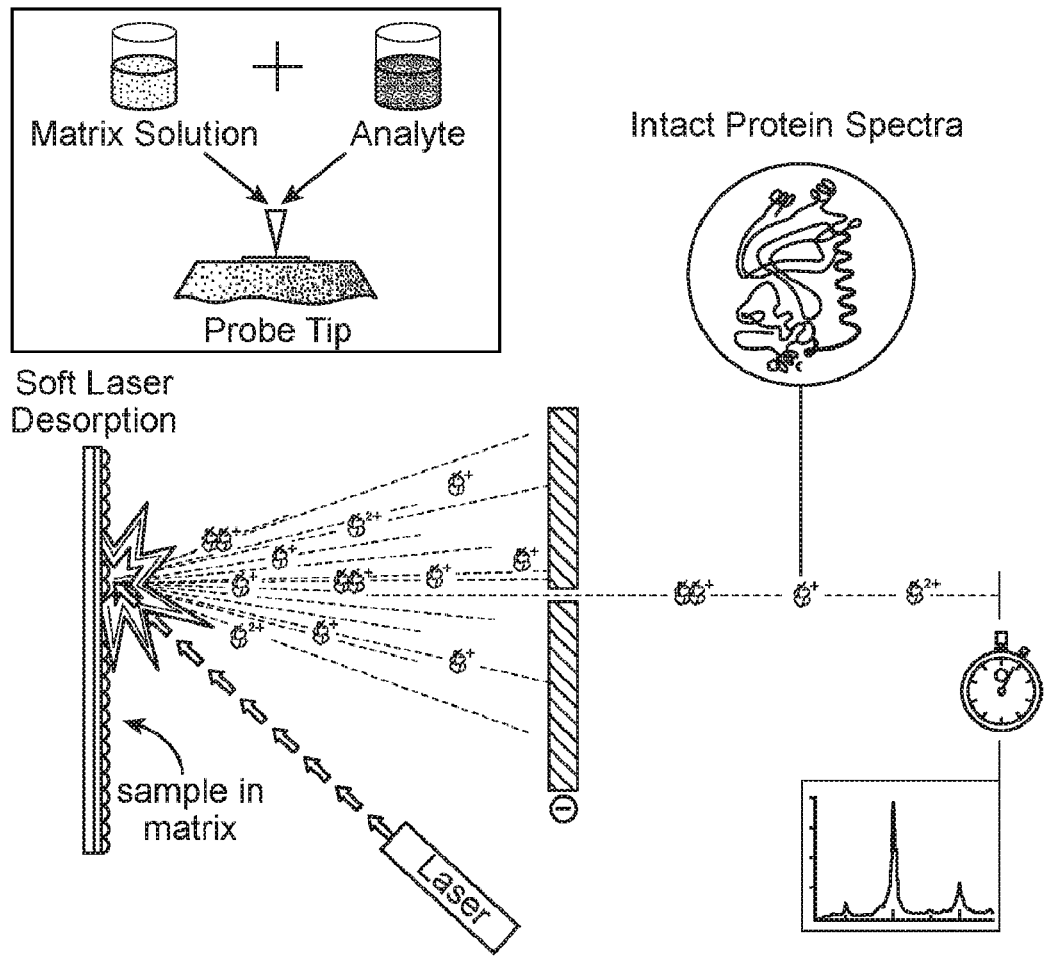
FIG. 1. (Prior Art) Conventional MALDI TOF mass spectrometry process. A liquid MALDI matrix solution is mixed with the analyte directly on a plate that can be inserted into the mass spectrometer.
Figure 2:
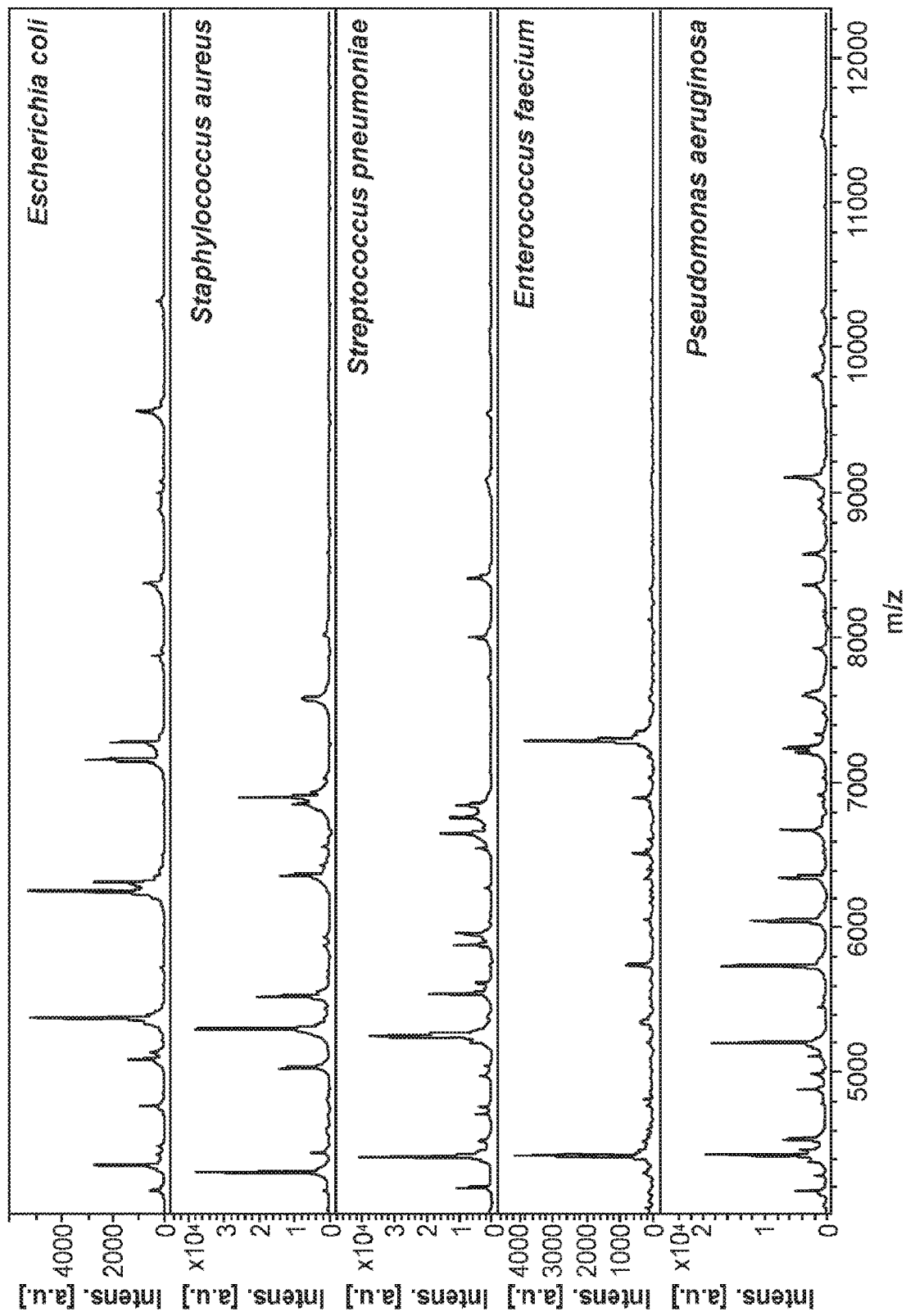
FIG. 2. (Prior Art) MALDI TOF mass spectrometry bacterial fingerprints illustrate the capability of MALDI TOFMS.
Figure 3:
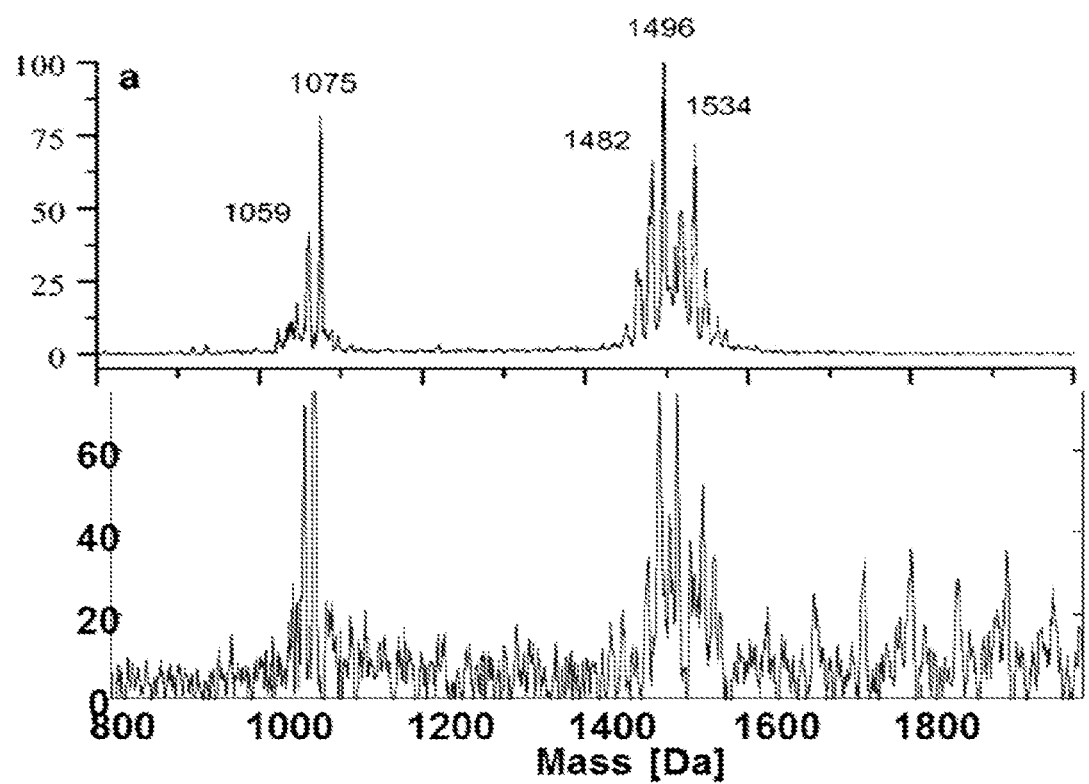
FIG. 3. (Prior Art) Comparison of spectra from Aerosol MALDI mass spectrometry (bottom) and traditional MALDI (top) for *Bacillus* spores. The bottom spectrum is an average of 135 spectra, with each spectrum obtained from a single airborne *Bacillus* spore.

All reference numerals, designators and callouts in the figures are hereby incorporated by this reference as if fully set forth herein. The failure to number an element in a figure is not intended to waive any rights. Unnumbered references may also be identified by alpha characters in the figures and appendices.

FURTHER DESCRIPTION

Particular aspects of the disclosure are described below in considerable detail for the purpose for illustrating its principles and operation. However, various modifications may be made, and the scope of the disclosure is not limited to the exemplary aspects described.

FIG. 4 shows a process flow diagram 400 of a first exemplary aspect for generating MALDI matrix coated analyte aerosol particles in real-time. In FIG. 4, a MALDI matrix solution is provided in step 401. The MALDI matrix solution is nebulized in step 402 to form a first aerosol comprising MALDI aerosol droplets (Type 1 aerosol). In step 403, a sample aerosol stream (Type 2 aerosol) comprising analyte particles is provided. The Type 1 aerosol is then entrained into the Type 2 aerosol. The Type 2 aerosol may comprise particles in ambient air. Further, the Type 2 aerosol may contain at least some particles of biological origin.

The resulting stream comprising droplets of MALDI matrix solution and analyte particles may be optionally mixed in step 404 prior to entry into an acoustic coater. The aerosolized MALDI matrix and the analyte aerosol particles can be introduced to the mixing section using several methods depending upon the nature of the analyte, and the method used to aerosolize MALDI matrix material. As described above, the MALDI matrix aerosol can be entrained in the analyte aerosol stream. Alternately, the analyte aerosol can be entrained into a MALDI matrix aerosol.

An acoustic field is provided in the acoustic coater and causes the matrix aerosol to impact upon the sampled aerosol particles and coat the sampled aerosol particles in step 405. For the sake of clarity, an acoustic coater is a coating chamber that is configured to receive a first aerosol comprising a coating material and a second aerosol comprising analyte particles and under the influence of an acoustic field generated by a sonic transducer produces coated aerosol particles comprising a coating of first aerosol on second aerosol by impinging first aerosol on particles of second aerosol. If needed, upon exiting the acoustic coater, the coated aerosol particles flow through a tube or conduit of sufficient length to allow the solvent in the matrix solution to substantially evaporate in drying step 406. Optionally in step 406, the aerosol can be heated, preferably with infrared or microwave photons, to enhance the evaporation of the solvent. The analyte aerosol, now coated with matrix solution and dried, is then analyzed using an instrument such as an ATOFMS.

The aerosol particles to be analyzed are not limited to particles found in ambient air. For example, the head space in a fermenter could be analyzed for possible contaminants. It is often desired to know the specification of microbes in the air within a food or healthcare facility. Further, respired air from a person or other animal may be of interest to a clinician. The analyte particles in step 403 could comprise of microbes such as viruses, bacteria, algae or fungi. Alternately, the analyte particles could comprise of proteins and peptides present in respired air that originated in the lungs of the host. The analyte particles could also comprise of a mixture of microbes and proteins and peptides.

Nebulizing MALDI Matrix Aerosol

Figure 5:
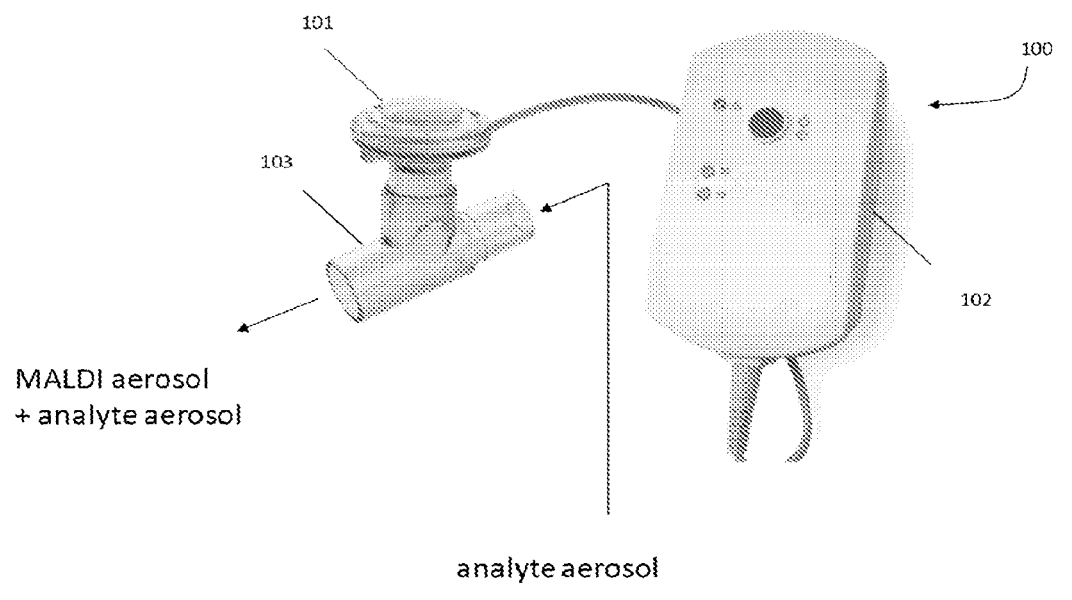

An exemplary nebulizer system 100 (FIG. 5), which can be used to nebulize MALDI matrix solution, and produce an aerosol of the MALDI matrix (Type 1 aerosol) in step 402 is provided by Aerogen (Ireland). This nebulizer is operated using an Aeroneb Pro controller. The nebulizer is designed to produce an aerosol without impacting the MALDI matrix's integrity or concentration. The nebulizer system produces a fine droplet, low-velocity aerosol without requiring a separate air compressor. In FIG. 5, the MALDI matrix solution is added to the nebulizer unit 101 that is controlled by controller 102. The nebulizer unit can hold up to 10 ml of MALDI solution and is attached to a T-piece 103. More typically, the nebulizer unit can be configured to hold less than 1 ml of MALDI solution to prevent waste. The nebulizer is capable of converting the MALDI liquid solution to an aerosol comprising of particles of mean diameter in the range of 2.5 to 6 micrometers (VIVID, volume mean diameter). The nebulizer is also capable of producing MALDI droplets of <3 micron size MMAD (mass median aerodynamic diameter). Nebulizer unit 101 consists of a domed aperture plate with precision-formed holes that control the size of the aerosol droplets, and a vibrational element that creates micro-pumping action to aerosolize the MALDI liquid solution. When power is supplied by the controller to the vibrational element, the aperture plate vibrates at over 100,000 times per second. This rapid vibration causes each aperture to act as a micropump, drawing liquid through the holes to form consistently sized droplets. Additional details on Aerogen nebulizers are provided in U.S. Pat. Appl. US20090134235. Aeroneb sells various models which are designed with different sized holes in the vibrating orifice plate to produce droplets of varying predetermined mean particle diameter. When the MALDI matrix solution comprises high volatility solvents such as methanol, the size of the particles in the Type 1 aerosol could decrease to about 0.5 micrometers because of vaporization of the solvent.

One additional advantage of this type of nebulizer is the ability to independently control the number of particles (or the mass of particles) generated as a function of time. FLIR Systems (Wilsonville, Oreg.) sells a nebulizer and controller that allows the particle generation rate to be controlled. If the particle density of analyte particles is known or measured, for example by an aerodynamic particle sizer (APS model 3320 from TSI, Inc., Minneapolis, Minn.), the mass of coating particles can be adjusted in real time to the desired ratio of coating particles to analyte particles.

It is desired to have each analyte particle coated by at least an equal mass of matrix solution, but preferably up to 10 times the mass the analyte particle. Accordingly, in one aspect, the matrix solution is nebulized at a mass flow rate equal to five to ten times the analyte aerosol dry mass flow rate. Since the mean spacing of the particles would be significantly greater than the mean particle diameter, agglomeration of the MALDI liquid particles would be minimal.

Typically, nebulizer system 100 is used to provide aerosolized medication to treat lung diseases such as asthma. For the application disclosed here, however, as shown in FIG. 5, analyte aerosol (for example, entrained in air) enters at one end of the T-piece 103, contacts aerosolized MALDI solution, and exits through the other end of T-piece 103. To prevent the aerosolized MALDI from exiting through the entry end of T-piece 103, an in-line check valve that allows flow in only one direction can be installed at or near the entry end of T-piece 103. Suitable check valves are commercially sold by vendors such as Cole Parmer, Cambridge Reactor Design, and Upchurch Scientific.

Another alternative to the Aeroneb nebulizer is the I-neb AAD System supplied by Philips Healthcare (Andover, Mass.). This nebulizer comprises a small, battery powered, lightweight and virtually silent device designed to significantly reduce the inconvenience of conventional nebulizer/compressor therapy, while delivering a precise, reproducible dose of the aerosol. The aerosol is created through vibrating mesh technology. The metering chambers can deliver a pre-set volume ranging from 0.25 to 1.4 ml, with a residual of about 0.1 ml.

The MALDI matrix could include 3,5-dimethoxy-4-hydroxycinnamic acid (sinapinic acid), α-cyano-4-hydroxycinnamic acid (α-cyano or α-matrix) and 2,5-dihydroxybenzoic acid (DHB) as described in U.S. Pat. No. 8,409,870. A suitable solvent and trifluroacetic acid are generally added to these matrix materials.

The MALDI matrix may further comprise a tag that interacts with the sampled aerosol such that it makes detection more specific. The tag may be either a mass tag, or an optical tag such as a protein stain. Mass tags could comprise smart polymers such as self-immolative polymers. When subjected to an external stimuli or trigger such as ionization in a mass spectrometer, these polymers disassemble or cleave in a structured fashion to release molecular fragments, leaving behind a part of the starting polymer. The released molecules could be more volatile than the starting polymer. The polymer could also sequentially undergo head-to-tail depolymerization to its monomers. When an analyte particle of biological origin is coated with a MALDI matrix comprising a self-immolative polymer tag, and fragmented in an ATOFMS, sequence information can be obtained from fragmentation of the protein (analyte) and quantification data from fragmentation of the tag.

The disclosed devices and methods are not limited to MALDI matrix coatings of bio aerosol particles. Any type of coating, such as a liquid protein stain, could be applied to bio aerosol or non-bio aerosol particles to enhance the ability to distinguish a characteristic of particles comprising an aerosol, or otherwise alter the particles of an aerosol in a manner that makes some or all of the particles comprising the aerosol more useful. A protein stain may be used to distinguish which particles are of biological origin from those that are of other composition, such as a mineral. Gel stains for detection of specific classes of proteins are provided by ThermoFisher Scientific (Grand Island, N.Y.) and Sigma Aldrich (St. Louis, Mo.). For example, a cell staining solution can be used to coat bio aerosol particles on-the-fly to determine if a cell or cells in the bio aerosol was viable or not via a color or florescence measurement. The color or fluorescence of the coated particles can be measured to assess the viability of the cells. A number of single cell measurements can be accomplished using stains. Examples of stains include, but are not limited to vital stains (trypan blue or propidium iodide for eukaryotic cells) and supravital stains (e.g. New Methylene Blue and Brilliant Cresyl Blue for reticulocyte staining). A mixture of liquids may also be used for coating analyte particles.

The MALDI matrix material need not be in the form of a liquid. It could be a slurry or even constitute fine metal powders such a cobalt powders. These powders are preferably less than 1 micrometers in size, and more preferably less than 0.01 micrometers size. In addition, conductive materials such as graphite, carbon nanotubes and fullerene derivatives can also be used as MALDI matrices. A mixture of conductive metal and non-metal powders may also be used.

Analyte Aerosol

With respect to Type 2 aerosol (FIG. 4), this aerosol may comprise of one or more types of analyte particles. As one example, Type 2 aerosol could include exhaled breath particles (EBP) found in exhaled air of humans. The volume of air exhaled during breathing in healthy adults is typically between 1-2 liters, which includes a normal tidal volume of about 0.5 liters. Humans produce exhaled breath particles (EBPs) during various breath activities, such as normal breathing, coughing, talking, and sneezing. One study found that EBP concentrations from mechanically ventilated patients during normal breathing were in the range 0.4 to 2555 particles/breath or 0.001 to 5 particles/mL (Wan G-H, Wu C-L, Chen Y-F, Huang S-H, Wang Y-L, et al. (2014), "Particle Size Concentration Distribution and Influences on Exhaled Breath Particles in Mechanically Ventilated Patients," PLoS ONE 9(1): e87088). In addition, the size of the EBP's were below 5 micrometers, and 80% of them ranged from 0.3 to 1.0 micrometers. Exhaled particle size distribution has also been reported to fall between 0.3 and 2.0 micrometers. The mean particle sizes of EBPs were less than 1 micrometer during normal breathing, and 1 to 125 micrometers during coughing. Further, 25% of patients with pulmonary tuberculosis exhaled 3 to 633 CFU (colony forming unit) of *Mycobacterium tuberculosis* when coughing, and levels of this pathogen primarily ranged 0.6 to 3.3 micrometers. These bacteria are rod shaped and are about 2 to 4 micrometers in length and about 0.2 to 0.5 micrometers in width.

Another example for Type 2 aerosol is biological aerosols that could be the product of biological terrorist threats. The ambient air within critical infrastructures, such as international airports or in subways, can be directly sampled. If needed, a sample of Type 2 aerosol may be captured using suitable means such a sampling bag or other similar enclosures. The particles could also derive from a liquid sample obtained from a wet-wall cyclone or similar device that has been subsequently re-aerosolized. An example of a wet-wall cyclone is the SpinCon II (Innovaprep, Drexel, Mo.). The particles in these aerosols could include, but are not limited to anthrax, Ebola virus, ricin, and botulinum toxin. In this case, it may be beneficial to use a nebulizer that aerosolizes MALDI matrix solution into air as shown flow diagram 500 in FIG. 6. One example of a suitable nebulizer is the VIOS Pro Aerosol Delivery system supplied by Pari Respiratory Equipment Inc., (Midlothian, Va.). The MALDI matrix solution is provided in step 501 and is aerosolized into an air stream supplied by an air pump or compressor in step 502. In contrast to flow diagram 400, the air stream containing Type 1 aerosol (MALDI matrix solution) is then used to entrain Type 2 aerosol (analyte) provided in step 503. The type 2 aerosol could be injected into the Type 1 aerosol stream using a syringe or a pump. Alternately, air containing Type 1 aerosol could be used to flush a sampling bag or enclosure containing a suitable sample of Type 2 aerosol.

The resulting stream comprising droplets of MALDI matrix solution and analyte particles may be optionally mixed in step 504 prior to entry into an acoustic coater for coating in step 505.

Mixing the Type 1 and Type 2 aerosol must be done carefully so as to not cause surface deposition of the aerosol as a result of intense turbulence. Accordingly, in the mixing chamber, the mixing flow tube diameter D and mean velocity V should be chosen such that the Reynolds Number ($\rho DV/\mu$) is less than approximately 2000, where $\rho$ is the density of air and $\mu$ is the viscosity of air. Mixing may be induced by a static mixing plate (for example, supplied by Charles Ross and Son Company, Hauppauge, N.Y.), or by a static grid mixer (for example, supplied by Stamixco AG, Wollerau, Switzerland). These devices induce a modest level of turbulence. Intense turbulence will indeed cause mixing of the aerosol, but it is in undesired as it will also result in deposition of aerosol on the tube walls. Low intensity turbulence achieves the desired mixing of Type 1 and Type 2 aerosol while minimizing deposition of aerosol on the walls of the mixing chamber.

The aerosolized MALDI matrix and the analyte aerosol particles can be introduced to the mixing section using suitable methods depending upon the nature of the analyte and the method used to aerosolize MALDI matrix material. In either flow diagram 400 or 500, optionally, a sheath fluid (as used in flow cytometers) may be added though the walls of the mixing section, which is upstream of the acoustic coater, to reduce or eliminate deposition of the aerosol. The mixed aerosol then enters the acoustic coater. A typical sheath fluid for most applications would be air, suitably filtered to remove all or nearly all particulates.

A typical mixing component would consist of an inlet, a static mixer (mixing chamber) oriented laterally across the flow, followed by a straight tube out, in which the flow mixes and then slowly re-laminarizes. Re-laminarization of the flow can be enhanced by contracting the flow through a section of tube that has a small decrease in tube diameter.

An acoustic field is maintained in the acoustic coater, and causes the matrix aerosol to impact upon the sampled aerosol particles and coat the sampled aerosol particles in step 505. If needed, upon exiting the acoustic coater, the coated aerosol particles flow through a tube or conduit of sufficient length to allow the solvent in the matrix solution to substantially evaporate in drying step 506. Optionally in step 506, the aerosol can be heated, preferably in a spatially uniform manner with infrared or microwave photons, to enhance the evaporation of the solvent. The aerosol, now coated with matrix solution and dried, is then analyzed using an instrument such as an ATOFMS suitably modified with the appropriate ionization laser wavelength and an analyzer mass range that is typical of MALDI ATOFMS.

The nebulizing step 502 can produce MALDI particles in air with concentrations varying from 440 mg/min to 590 mg/min. Nebulizers used in step 502 may also be chosen to produce MALDI particles in air with concentrations between 100 mg/min to 600 mg/min. The mass median diameter (MMD) of the particles could vary from 3.7 to 4.4 micrometers. The mass median diameter (MMD) of the particles may also vary from <1 micrometer to 5 micrometer depending on the type and model of the nebulizer that is used in step 502. The mass fraction of particles below 5 micrometers could vary from 67% to 75%. The nominal air flow from the compressor will depend on the model and type of nebulizer selected, and will typically be below 5 liters per minute.

Acoustic Coating

The MALDI aerosol (Type 1 aerosol) could generally be comprised of liquid particles with median mass diameters (MMD) between 3 and 4 micrometers. The analyte aerosol (Type 2) can comprise of particles, such as exhaled breath particles with median mass diameters between 0.3 to 4 micrometers. The next step involves the selective coating of the analyte aerosol by the MALDI liquid particles in steps 405 or 505. This is particularly challenging because the size of the MALDI particles is somewhat comparable to that of the analyte particles, and more so if the analyte particles are biological matter such as the rod shaped *Mycobacterium tuberculosis*. Further, ATOFMS instruments such as those previously supplied by TSI, Inc. are generally designed to receive particles ranging from 0.03 to 3 micrometers in size. However, other types of ATOFMS instruments, such as those under development by BiosparQ, BV (Leiden, The Netherlands) are designed to receive particles up to 10 micrometers. A suitable coating method should preferably coat the analyte particle (for example with a coating thickness of at least one micrometer but less than 5 micrometers thick) with the MALDI matrix particles without increasing the size of the coated analyte particles to greater than 10 micrometers.

The inventors have unexpectedly discovered that methods used to agglomerate fine particles having the same composition (e.g. fly ash) during environmental clean-up of pollutant particles from air, can be modified to selectively coat the analyte particles using the MALDI matrix liquid particles in steps 405 or 505. One such method commonly known as acoustic agglomeration is described in U.S. Pat. No. 4,475,921, which discloses that particles in the 0.5 micrometers to 5 micrometers range can be agglomerated to yield particles of size greater than 5 micrometers. This technique is useful for removing fine pollutant particles (such as coal particles) from the exhaust of power plants. The larger particles can be removed using conventional methods such as venturi scrubbers.

The sonic agglomerator disclosed in U.S. Pat. No. 4,475,921 typically consists of a cylindrical chamber with flat end-walls. The gas stream with entrained fine particles enters through one end and exists at the opposite end. A sonic generator is disposed at the entrance wall of the chamber and applies acoustic energy to the chamber. The acoustic energy vibrates the particles to cause them to move against one another and agglomerate. Resonant acoustic energy of two or more different frequencies can be applied simultaneously to the chamber. The optimum acoustic frequency for vibrating a particle increases with decreasing particle size. Acoustic energy can be directed along the length of the chamber. Acoustic energy can also be directed perpendicular to the flow of gas into the chamber. When two waves are 90 degrees out of phase, the particles move in circular motion along the length of the chamber and provide more effective agglomeration. The sonic generator consists of a driver which generates electrical signals of closely controlled frequencies, a sonic transducer which converts the electrical signals to sonic energy, and a tube which couples the transducer to the inlet wall of the chamber. The driver is controlled to produce signals of frequencies that create sound waves of defined wavelengths within the chamber. Wavelengths are selected to correspond to the acoustic resonant mode of the chamber. When using sound intensity of about 140 dB relative to the hearing threshold of $10^{-16}$ watts per cm$^2$, the time required to agglomerate particles in the 0.5 to 5 micron range was less than 10 s. The average residence time of the gas in the chamber was about 6 s (with a velocity of about 1 ft/s).

U.S. Pat. No. 7,150,779 discloses an acoustic field that is frequency and/or amplitude modulated. The frequency is modulated in the range from 20 kHz to 1 GHz, and the amplitude to about 200 dB (referenced to 20 micro Pascals). Alternately, the frequency of the acoustic field varies from about 50 Hz to about 15 kHz, and the amplitude from 130 to 175 dB. While flowing gas at a velocity of 3 ft/s, and applying an acoustic field of 150 dB at approximately 600 Hz, particles in the 0.5 to 2 micron (micrometer) range, could be agglomerated to 2 to 5 microns. The modulated acoustic field could be produce using a mechanical oscillator and a shaft that connects the oscillator to an acoustic plate.

U.S. Pat. No. 8,387,363 discloses good separation of particulates in automobile exhaust using sinusoidal sound waves while using frequencies of 25 and 45 Hz and a loud speaker power of 28 and 12 W. The separation efficiency was found to be proportional to the power of the sound source. The frequency was found to have a minor effect.

Without being limited by any theory, the inventors believe that acoustic coating of Type 2 aerosol (analyte) with Type 1 aerosol (MALDI matrix) in steps 405 or 505 can be accomplished at lower sound amplitude levels, preferably less than 140 dB relative to the hearing threshold of $10^{16}$ watts per cm$^2$, in one example. As opposed to the particulate removal schemes described above, the primary objective in steps 405 or 505 is to obtain coated analyte particles, and to avoid unnecessary agglomeration of the coated analyte particles. In the particulate removal schemes, the objective was to agglomerate fine pollutant particles into larger particles and remove them from the air exhaust streams using conventional means. In contrast, here, the Type 1 aerosol comprises liquid particles that would tend to collapse when they impact each other. Coating of analyte particles is accomplished when the Type 1 aerosol particles impact with a Type 2 aerosol particles (analyte). An acoustic coater for use in steps 405 or 505 a shown in in FIG. 4 or FIG. 6 could comprise a cylindrical chamber three inches in diameter and about 10 cm in length. At an air flow rate of about 5 liters per minute, the residence time in the chamber would be about 6 s. Alternately, a cylindrical chamber that is 8 cm in diameter and 20 cm in length may also be used; with an air flow rate of 3 liters a minute, the residence time in the chamber would be about 10 s. An acoustic field of about 140 dB would urge the Type 1 aerosol particles to impact upon Type 2 aerosol, and coat the particles of Type 2 aerosol. The intensity of the sound field is expected be equivalent to less than 10 Watts in the exemplary acoustic coater. Accounting for inefficiencies in converting electrical signals to sound, a power source of <20 Watts may be sufficient. The inventors further believe that the acoustic field could be applied 90 degrees out of phase, to enable excess MALDI matrix material to condense out of the air stream as the particles move in circular motion along the length of the acoustic coater leaving a high fraction of coated analyte particles in the air stream that exits the acoustic coater.

A noise canceling system may be used to cancel the noise produced by acoustic coater during operation and to make the device quiet for indoor operation. Alternately, the acoustic coater may be operated in the ultrasonic range (typically >20 kHz). An ultrasonic transducer, for example, a piezoelectric transducer may be used to apply ultrasonic energy to the acoustic coater (chamber). Suitable piezo electric transducers are supplied by Steiner & Martins, Inc. (Doral, Fla.).

The size of the MALDI matrix coated particles is expected to be less than 20 micrometers, and more preferably less than 10 micrometers.

The acoustic coater may be considered to be a replaceable part in the acoustic MALDI matrix coating device or other generalized coating devices, or in the MALDI ATOFMS.

The optional drying step in FIG. 4 and FIG. 6 is performed by direct contact of the coated particles with a hot surface. Alternately, infrared or microwave radiation can be used to heat the coated aerosol to accelerate the drying of the coated particles. Thermally heated walls may also be used, but care must be taken with temperature profiles so as not to induce significant thermal instabilities in the flow. A preferable configuration is to orient the aerosol to flow vertically downward in a laminar flow regime while heat is being gently applied.

Figure 7:
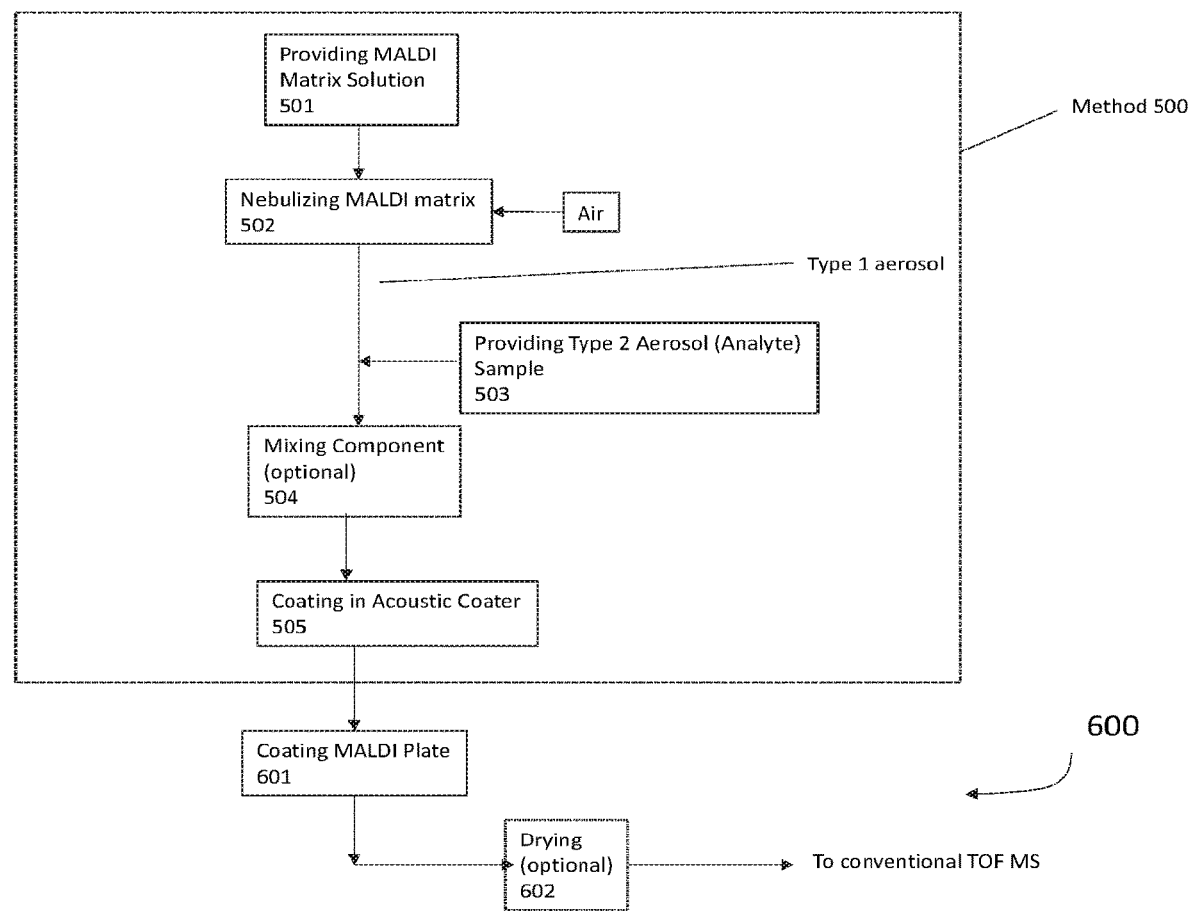
FIG. 7. Schematic diagram of modified method to coat conventional MALDI plates using MALDI coated aerosol analyte particles.

In another aspect, the coating methods disclosed here can also be modified to improve the detection efficiency and throughput of conventional MALDI TOF spectrometers described in FIG. 1. In this modified process 600 described in FIG. 7, the sample analyte aerosol particles are coated with a MALDI matrix aerosol using methods 400 or 500 described in FIG. 4 or FIG. 6; however, the coated analyte aerosol particles are not directly routed to a mass spectrometer. Instead, the MALDI coated analyte aerosol particles are first deposited onto a MALDI plate in step 601 using an aerosol impactor; for example, the impactor described in U.S. Pat. No. 7,591,980 may be used. The coated, deposited particles form a coating that is subsequently dried (step 602) if required and the coated plate is then analyzed using a conventional TOF mass spectrometer. FIG. 7 shows the modification to the method 500; method 400 can also be similarly modified to coat MALDI plates. In method 600, a drying step may be employed prior to coating a MALDI plate if needed.

The MALDI matrix solution generally comprises an organic matrix material, an acid, and a solvent. Commonly used organic matrix materials in the MALDI matrix solution are 2,5-dihydroxybenzoic acid, alpha-cyano-4-hydroxycinnamic acid, 3,5-dimethoxy-4-hydroxycinnamic acid and 2-mercapto-4, 5-dialkylheteroarene. The MALDI matrix solution could comprise of other matrix molecules including 1,8-dihydroxyanthracen-9(10H)-one, 3-methoxy-4-hydroxycinnamic acid, 2,4,6-trihydroxyacetophenone, 2-(4-hydroxyphenylazo)-benzoic acid, trans-3-indoleacrylic acid, 4-hydroxy-3-methoxybenzoic acid, 6-aza-2-thiothymine, 2-amino-4-methyl-5-nitropyridine, 4-nitroaniline, 1,5-diaminonaphthalene, 5-fluorosalicylic acid, 5-chlorosalicylic acid, 5-bromosalicylic acid, 5-iodosalicylic acid, 5-methylsalicylic acid, 5-aminosalicylic acid, and 1,8-diaminonaphthalene.

Commonly used solvents in the MALDI matrix solution include acetonitrile, water, ethanol, methanol, propanol, and acetone. Other solvents including chloroform, isopropyl alcohol, tetrahydrofuran, and toluene may also be used.

Commonly used acids in the MALDI matrix solution include hydrochloric acid, trifluroacetic acid, formic acid, and acetic acid.

Figure 8:
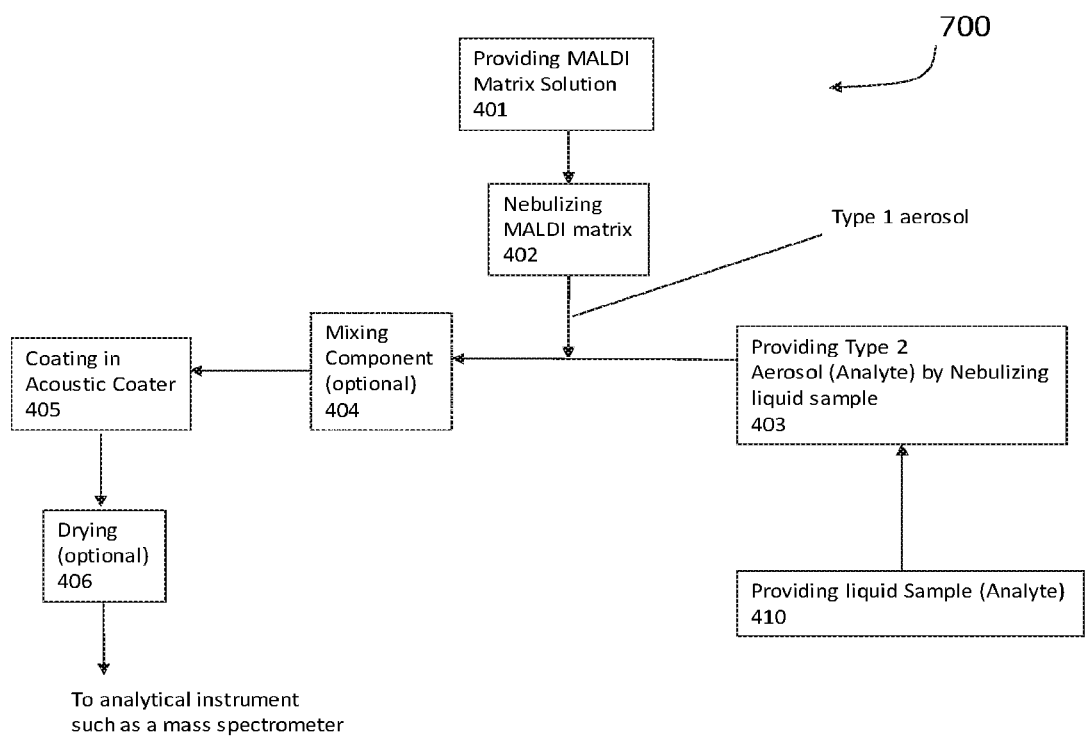
FIG. 8. Schematic diagram of modified FIG. 4. that shows nebulization of a liquid sample to form Type 2 aerosol with analyte particles.

In some instances, the analyte particles of interest may be contained in a liquid sample. The exemplary schematic diagrams shown in FIG. 4 and FIG. 6 may be modified to nebulize the liquid sample to provide the Type 2 aerosol. As shown in FIG. 8, which is a modification of FIG. 4, a liquid sample provided in step 410 in process 700 is nebulized using suitable nebulizers (as previously described in this disclosure) to provide the Type 2 sampled analyte in step 403. The schematic diagram shown in FIG. 7 may also utilize this modification. The Type 1 aerosol is then entrained into the Type 2 aerosol. Alternately, the Type 2 aerosol may be entrained into the MALDI matrix aerosol. Liquid samples comprising biological molecules suitable for analysis by MALDI time-of-flight mass spectrometry, could be obtained from the environment, from humans (often termed a clinical sample), from animals, or from a process that is part of a food or drug manufacturing operation. Examples of clinical samples include urine, saliva, sputum, and blood. An example of an analysis may be detection and identification of an organism causing a urinary tract infection, whereby the organism causing the infection is present in the urine sample. Some pre-treatment of the sample may be required; for example, salts in the sample may need to be removed by filtering the sample, washing the filter to remove the salts, and then re-suspending the organisms in a liquid prior to nebulization. Other samples, such as stool samples, may be suspended in liquid, and then analyzed similarly.

When noise cancelling systems and methods are employed as previously described, the cancelling noise is generated 180 degrees out of phase relative to the acoustic coater source. Typically, noise is generated at the same frequency as the coater's acoustic source.

The Abstract is provided to comply with 37 C.F.R. § 1.72(b), to allow the reader to determine quickly from a cursory inspection the nature and gist of the technical disclosure. It should not be used to interpret or limit the scope or meaning of the claims.

Although the present disclosure has been described in connection with the disclosed forms of practicing it, those of ordinary skill in the art will understand that many modifications can be made thereto without departing from the spirit of the present disclosure. Accordingly, it is not intended that the scope of the disclosure in any way be limited by the above description.

REFERENCES

1. Brown, R. S.; Lennon, J. J., Mass resolution improvement by incorporation of pulsed ion extraction in a matrix-assisted laser desorption/ionization linear time-of-flight mass spectrometer. (1995) Anal. Chem. 67 (13): 1998-2003.
2. Carbonnelle, E., Mesquita, C., Bille, E., Day, N., Auphin, B., Beretti, J.-L., Ferroni, A., Gutmann, L., Nassif, X. MALDI-TOF mass spectroscopy tools for bacterial identification in clinical microbiology laboratory, Clin Biochem (2010), doi: 10.1016/j.clinbiochem.2010.06.017.
3. Cherkaoui, A., Hibbs, J., Emonet, S., Tangomo, M., Girard, M., Francois, P. and Schrenzel, J., Comparison of Two Matrix-Assisted Laser Desorption Ionization-Time of Flight Mass Spectrometry Methods with Conventional Phenotypic Identification for Routine Identification of Bacteria to the Species Leve.l (2010) J. Clin. Microbiology, doi:10.1128/JCM.01881-09, p. 1169-1175.
4. Cotter, Robert J. (1997). Time-of-flight mass spectrometry, Instrumentation and Applications in Biological Research, American Chemical Society Professional Reference Books.
5. Cotter, Robert J. (1994). Time-of-flight mass spectrometry, American Chemical Society Symposium Series 549.
6. Danielewicz, M. A., Anderson, L. A. and Franz, A. K., Triacylglycerol profiling of marine microalgae by mass spectroscopy. (2011) J. Lipid Res., 52, 2101-2108.
7. Hathout, Y., Demirev P. A., Ho, Y.-P.,Bundy, J. L., Ryzhov, V., Sapp, L., Stutler, J., Jackman, J., and Fenselau, C., 1999, "Identification of *Bacillus* Spores by Matrix-Assisted Laser Desorption Ionization-Mass Spectrometry." App. and Env. Microbiollogy, V.65, No. 10, pp. 4313-4319.Jackson, S., Mishra, S. and K.
8. Karas, M.; Bachmann, D.; Bahr, U.; Hillenkamp, F. (1987). "Matrix-Assisted Ultraviolet Laser Desorption of Non-Volatile Compounds". Int. J. Mass Spectrom. Ion Processes 78: 53-68.
9. Knochenmuss R (2006). "Ion formation mechanisms in UV-MALDI". Analyst 131 (9): 966-986.
10. Stowers, M. A. et al., 2000, Application of matrix-assisted laser desorption/ionization to on-line aerosol time-of-flight mass spectrometry, Rapid Commun. Mass Spectrom., 14, 829-833.
11. van Wuijckhuijse, A. L., et al., 2004, Matrix-assisted laser desorption/ionisation aerosol time-of-flight mass spectrometry for the analysis of bioaerosols: development of a fast detector for airborne biological pathogens, 36 (5/6), P 677-68.
12. van Wuijckhuijse, A. L., and Call, C., Real-time MALDI TOF MS analysis of biological aerosols and contaminated paper dust with the BiosparQ™ detector. (2010) Proceedings from the 10th International Symposium from the Protection against Chemical and Biological Warfare Agents, Stockholm, Sweden.

What is claimed is:

1. A method for coating sampled aerosol particles, the method comprising:
   aerosolizing a coating material to form a first aerosol comprising liquid particles;
   providing a sampled aerosol containing analyte particles to form a second aerosol;
   providing an acoustic coater to receive said first aerosol and said second aerosol; and,
   providing an acoustic field to said acoustic coater to urge said first aerosol to impinge upon particles of said second aerosol on-the-fly to form coated aerosol particles comprising a coating of first aerosol on said second aerosol particles wherein the coating material comprises matrix assisted laser desorption ionization matrix solution comprising at least one of hydrochloric acid, trifluroacetic acid, formic acid, and acetic acid.

2. The method of claim 1 wherein the sampled aerosol is collected from the head space of a fermenter.

3. The method of claim 1 wherein the sampled aerosol is collected from ambient air.

4. A method for identifying the analyte particles present in a sampled aerosol, the method comprising:
   providing matrix assisted laser desorption ionization matrix coated sampled aerosol particles according to claim 1;
   coating a matrix assisted laser desorption ionization plate with matrix assisted laser desorption ionization matrix coated sampled aerosol particles; and,
   analyzing the coating comprising matrix assisted laser desorption ionization matrix coated sampled aerosol particles in a mass spectrometer.

5. The method of claim 4 further comprising a drying step to dry said coating prior to analyzing in the mass spectrometer.

6. A method for coating sampled aerosol particles with a coating material, the method comprising:
   aerosolizing a coating material comprising at least one of solid particles and a mixture of solid particles to form a first aerosol;
   providing a sampled aerosol containing analyte particles to form a second aerosol;
   providing an acoustic coater to receive said first aerosol and said second aerosol; and,
   providing an acoustic field to said acoustic coater to urge said first aerosol to impinge upon particles of said second aerosol to form coated aerosol particles comprising a coating of said first aerosol on particles of said second aerosol.

7. The method of claim 6 wherein said solid particles comprise metal powders of particles size less than 1 micrometer.

8. The method of claim 6 wherein said mixture comprises metal and non-metal powders.

9. The method of claim 7 wherein said metal powders comprise cobalt powders.

10. A method for identifying analyte particles present in a liquid sample, the method comprising:
    aerosolizing a coating material to form a first aerosol comprising liquid particles wherein the coating material comprises matrix assisted laser desorption ionization matrix solution;

aerosolizing a liquid sample to form a second aerosol comprising analyte particles;

providing an acoustic coater to receive said first aerosol and said second aerosol;

providing an acoustic field to said acoustic coater to urge said first aerosol to impinge upon particles of said second aerosol on-the-fly to form coated aerosol particles comprising a coating of first aerosol on said analyte particles; and, analyzing said coated analyte particles in a mass spectrometer.

11. The method of claim 10 wherein the mass spectrometer is an aerosol time of flight mass spectrometer (ATOFMS).

* * * * *